United States Patent
Ring

(10) Patent No.: US 8,262,860 B2
(45) Date of Patent: Sep. 11, 2012

(54) PAPER PULP PRE-PROCESSOR

(75) Inventor: Gerard J. F. Ring, Custer, WI (US)

(73) Assignee: WiSys Technology Foundation, Madison, WI (US)

( * ) Notice: Subject to any disclaimer, the term of this patent is extended or adjusted under 35 U.S.C. 154(b) by 928 days.

(21) Appl. No.: 11/844,818

(22) Filed: Aug. 24, 2007

(65) Prior Publication Data
US 2008/0066883 A1 Mar. 20, 2008

Related U.S. Application Data

(60) Provisional application No. 60/844,439, filed on Sep. 14, 2006.

(51) Int. Cl.
*D21F 1/06* (2006.01)
(52) U.S. Cl. .......... 162/259; 162/252; 162/263
(58) Field of Classification Search .......... 162/252, 162/253, 259, 263
See application file for complete search history.

(56) References Cited

U.S. PATENT DOCUMENTS

| | | | |
|---|---|---|---|
| 6,203,667 B1 * | 3/2001 | Huhtelin | 162/253 |
| 6,311,550 B1 | 11/2001 | Lehmikangas et al. | |
| 6,517,680 B1 * | 2/2003 | Fredlund et al. | 162/198 |
| 2005/0241786 A1 * | 11/2005 | Edwards et al. | 162/109 |

OTHER PUBLICATIONS

Weise et al., Papermaking Part 1, Stock Preparation from the Wet End, 2000, Fapet Oy, Book 8 Papermaking Science and Technology, p. 129-131 and 139-142.*
Tornberg et al., Process Control, 1999, Fapet Oy, Book 14 Papermaking Science and Technology, p. 58-61.*
McDermid, Fiber length, and Fiber Coarseness explained, 2003, Econotech, p. 1.*
Seborg et al., Process Dynamics and Control, 2004, John Wiley and Sons, $2^{nd}$ edition, p. 388-397 and 403-404.*
Gerard J.F. Ring, et al., Multiple Component Analysis of Fiber Length Distributions, Tappi Journal, Jan. 1997, vol. 78, No. 7, Norcross, GA, USA.
kajaaniFSA On-Line Fiber Length Analyzer, webpage retrieved Jul. 31, 2006, www.metsoautomation.com/atuomation/pp_prod.nsf/PrintView/DA0961BADDD7E38AC2256F420031DFF6.

* cited by examiner

*Primary Examiner* — Anthony Calandra
(74) *Attorney, Agent, or Firm* — Boyle Fredrickson, S.C.

(57) ABSTRACT

A pulp pre-processor for the papermaking industry uses pulp fiber analyzers to determine the distribution of fiber parameters, such as length, curl or coarseness from a feed source, such as recycled pulp, and mixes metered portions of pulp from augmenting pulp sources on an as-needed basis to provide a uniform distribution of a particular fiber parameter while maximizing use of recycled pulp.

7 Claims, 3 Drawing Sheets

PAPER PULP PRE-PROCESSOR

CROSS REFERENCE TO RELATED APPLICATIONS

The present application claims the benefit of U.S. Provisional Patent Application Ser. No. 60/844,439 filed on Sep. 14, 2006.

STATEMENT REGARDING FEDERALLY SPONSORED R & D

Not applicable

FIELD OF THE INVENTION

The present invention relates to papermaking and, in particular to a pulp pre-processor providing more uniform paper quality and having particular application for the manufacture of recycled paper.

BACKGROUND OF THE INVENTION

The process of making paper involves harvesting fibers from plants, typically trees, through a pulping process that separates the plant material into individual fibers. The resulting pulp fibers are diluted with 200 parts of water to one part fiber by weight. This fiber suspension, now referred to as stock, is supplied to a paper machine through a head box, which spreads the stock onto a moving wire to begin the process of de-watering the stock and consolidating the fibers into a formed paper sheet.

As water is drained from the forming sheet, individual fibers that were once relatively free to move independently become immobilized in a network of cellulose fibers held together by hydrogen bonding between the water and cellulose molecules. Water is then removed from the resulting sheet by mechanical pressing and then by drying until the finished sheet of paper is produced.

The production of paper has become more reliant on pulp that has been derived from waste paper recycled from many sources. Normally, recycled paper pulp is combined with un-recycled pulp to improve the quality of the resulting paper and to compensate for damage to the fibers of the recycled pulp that may occur during the recycling process. The large variation in the quality of recycled pulp effectively limits the amount of recycled pulp that may be added to the stock if a given paper quality is to be assured.

SUMMARY OF THE INVENTION

The present invention provides a pulp pre-processor that analyzes a pulp source, such as recycled pulp, and effects real-time correction of the pulp source by the addition of other pulp sources of known statistical characteristics. Real-time control can permit the addition of greater proportions of recycled pulp while still producing a uniform stock and, thus, uniform quality of paper. The present technique may also allow improved production on non-recycled paper by eliminating assumptions about pulp uniformity and allowing fine corrections of pulp consistency on a real-time basis.

Specifically then, the present invention provides a pulp pre-processor having a mixing cabinet and at least two pulp sources communicating with the mixing cabinet by means of controllable valves. Electronic pulp fiber analyzers associated with each of the two pulp sources provide corresponding signals measuring a statistical distribution of at least one physical parameter of the fibers of the pulp sources as delivered to the mixing cabinet. A controller receiving the signals from the electronic pulp fiber analyzers calculates a relative percentage of fiber from each of the two pulp sources necessary to produce a predetermined statistical distribution of fibers in the mixing cabinet. Based on this calculation, the controller provides real-time control signals to the valves to control them according to the calculated relative percentage.

Thus, it is one object of at least one embodiment of the invention to provide a more uniform stock by real-time adjustment of pulp percentages from multiple pulp sources.

One source may provide a distribution of fiber lengths relative to the other source that is skewed toward longer fiber lengths and the electronic pulp fiber analyzers may provide signals measuring statistical distributions of fiber length.

Thus, it is an object of at least one embodiment of the invention to control a fiber length distribution in the stock used to make paper by dynamically combining multiple sources having complex fiber length distributions.

Alternatively, or in addition, one source may provide a distribution of fiber curl relative to the other source that is skewed toward less fiber curl and the electronic pulp fiber analyzers may provide signals measuring statistical distribution of fiber curl.

Thus, it is another object of at least one embodiment of the invention to provide dynamic control of the distribution of fiber curl in papermaking stock.

The one source may alternatively or in addition provide for a distribution of fiber coarseness relative to the other source that is skewed toward greater fiber coarseness and the electronic pulp fiber analyzers may provide signals measuring statistical distributions of fiber coarseness.

Thus, it is another object of at least one embodiment of the invention to provide for more uniform pulp with respect to the parameter of fiber coarseness.

It is another object of at least one embodiment of the invention to allow use of variable pulp sources, such as from recycled paper, by allowing real-time "tuning" of the pulp fiber with respect to any one of: fiber length, curl, and coarseness.

The pulp pre-processor may further provide a third controllable valve leading from the mixing cabinet and a third electronic pulp fiber analyzer providing a third signal measuring a statistical distribution of at least one physical parameter of fibers of the pulp as it is delivered from the mixing cabinet and the controller may further control the relative proportions of the pulp from the two sources based on the third signal and the predetermined statistical distribution.

Thus it is an object of at least one embodiment of the invention to measure both the quality of the pulp being mixed and the resultant product so as to provide for improved control accommodating effects of the mixing process, transport delay, or errors in the other pulp fiber analyzers.

The pulp pre-processor may further include a third source and a third controllable valve leading to the mixing cabinet and a third electronic pulp fiber analyzer providing a third signal measuring a statistical distribution of at least one physical parameter of fibers of the pulp as delivered to the mixing cabinet from the third source and the controller may further control the relative proportions of the pulp from the three sources based on the predetermined statistical distribution.

Thus it is an object of at least one embodiment of the invention to provide for the correction of a feedstock pulp, for example, recycled fibers, in either of two control directions through the use of multiple augmenting pulp sources, for example, having longer fiber distributions and shorter fiber distributions with respect to a principal pulp source to be corrected.

The controller may control the relative proportion of the pulp from the two sources based on the third signal to maximize use of the third source within the constraint of the predefined statistical distribution.

Thus it is an object of at least one embodiment of the invention to provide a control strategy that may maximize the percentage contribution of one pulp source, for example, recycled pulp, with improved stock uniformity.

These particular objects and advantages may apply to only some embodiments falling within the claims and thus do not define the scope of the invention.

BRIEF DESCRIPTION OF THE INVENTION

DETAILED DESCRIPTION OF THE PREFERRED EMBODIMENT

Figure 1:
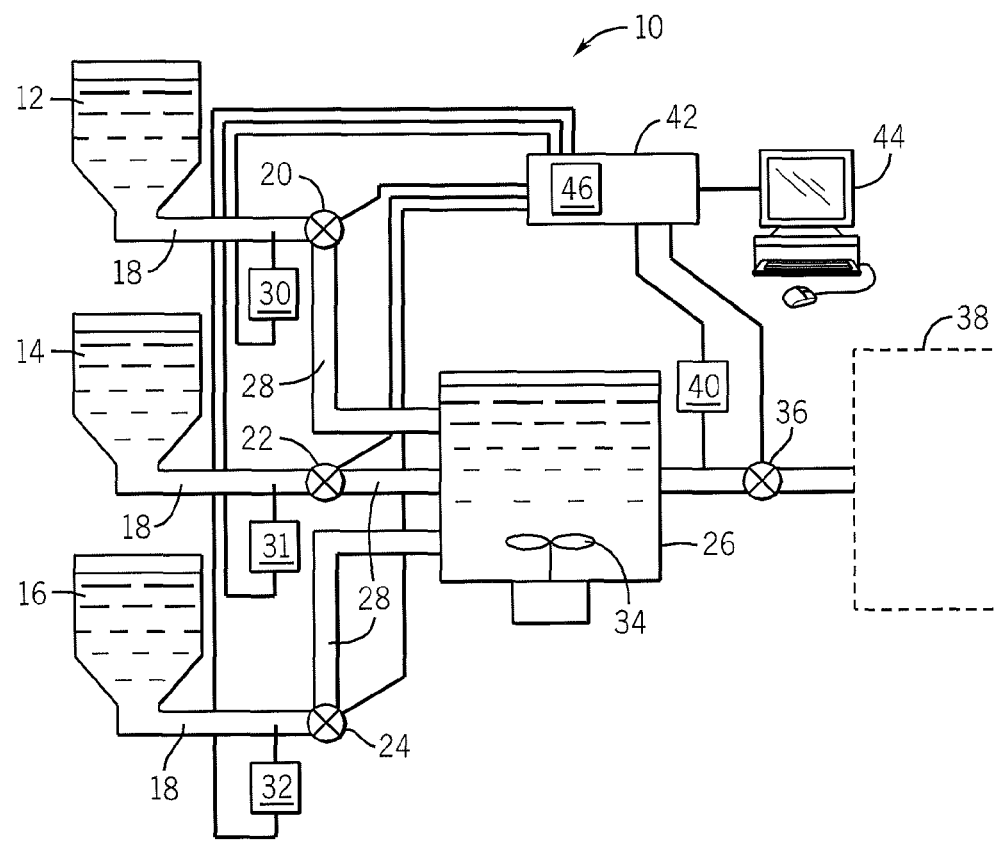
FIG. 1 is a block diagram of a first embodiment of a pulp pre-processor of the present invention employing three pulp sources combined in the mixing cabinet to provide improved fiber distributions under the control of a controller.

Referring now to FIG. 1, a pulp pre-processor 10 of the present invention may use three pulp sources 12, 14 and 16 being generally tanks containing cellulose fibers in water, for example, held in suspension by agitating impellers (not shown).

Each of the pulp sources 12, 14 and 16 connects by means of pipes 18 to respective metering devices 20, 22 and 24 which may, for example, be valve and pump combinations or metering pumps operating to control the volume of flow from the pulp sources 12, 14 and 16 into a mixing cabinet 26, joined to the metering devices 20, 22 and 24 by pipes 28.

Online pulp fiber analyzers 30, 31 and 32 sample the pulp flowing through each of pipes 28 from metering devices 20, 22 and 24 on a real-time basis to provide statistical distributions of fiber parameters including at least one or all of: fiber length, fiber curl and/or fiber coarseness. Suitable pulp fiber analyzers 30, 31, and 32 may be the "Kajaani FSA Online Fiber Length Analyzer" commercially available from Metso Automation of Helsinki, Finland. The operation of pulp fiber analyzers of this type is described in U.S. Pat. No. 6,311,550, hereby incorporated by reference.

The mixing cabinet 26 may include a mixing impeller 34 so as to mix and suspend the pulp from each of the pulp sources 12, 14, and 16 as metered through metering devices 20, 22, and 24. The combined pulp is then pumped from the cabinet 26 by metering device 36 to the head box of a papermaking machine 38 or a holding tank.

A fourth pulp fiber analyzer 40 may sample the pulp exiting the mixing cabinet 26, for example between the cabinet 26 and metering device 36 to monitor the combined fiber distributions.

Each of the pulp fiber analyzers 30, 31, 32, and 40 provide signals to a central controller 42 which in turn provides control signals controlling each of metering devices 20, 22, 24, and 36. The controller 42 may further receive commands from a terminal 44, for example, defining a desired pulp distribution and variance. A central controller 42 suitable for use in the present invention may be a Logix series controller commercially available from Rockwell Automation of Milwaukee, Wis., or other suitable device.

Figure 2:
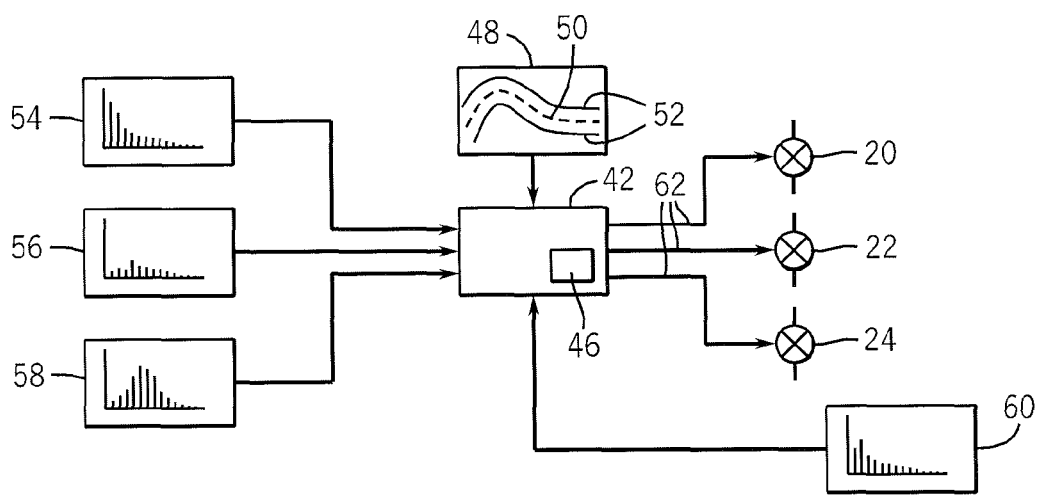
FIG. 2 is a schematic representation of data flow from electronic pulp analyzers associated with each of the pulp sources of FIG. 1 to the controller, and of control signal flow from the controller to control valves associated with each pulp source.

Referring to FIGS. 1 and 2, in the first embodiment, pulp source 14 may supply recycled paper pulp having varying fiber parameter distribution 56 reflecting a varying source of recycled fiber and affects on the fiber caused by recycling. In this example, pulp sources 12 and 16 provide augmenting pulp sources having distributions 54 and 58 intended to correct the fiber distribution 56 of the pulp of pulp source 14. For example, pulp sources 12 may be softwood fiber having a relatively higher concentration of long fibers greater than 3 millimeters, whereas pulp source 16 may supply hardwood fiber having a relatively higher concentration of short fibers and longest fibers of around 1 millimeter, meaning that the distribution of fibers in pulp sources 12 is skewed toward longer fibers with respect to the distribution of fibers of pulp source 16.

Examples of soft woods include Jack pine, Ponderosa pine, and redwood. Examples of hardwoods include sugar maple, silver birch, and aspen.

Referring now to FIG. 2, a controller 42 executes a stored control program 46 that receives a command data set 48 from a user, for example, entered through terminal 44. The command data set 48 provides, for example, a target distribution 50 showing a desired percent of fibers in each of a number of fiber length bins, for example, at every millimeter from one to seven millimeters. Typically, the target distribution 50 will provide for error bands 52 indicating a desired tolerance in the distribution obtained.

The controller 42 also receives corresponding distributions 54, 56 and 58 from each of the pulp fiber analyzers 30, 31 and 32, providing histograms counting numbers of fibers in each bin or providing weighted fiber counts (weighting the fibers according to their representative mass). In either case, the distributions 54, 56, and 58 provide the same domain and range as the desired distribution.

The controller will also receive a distribution 60 representing a sampling of the output of the tank from pulp fiber analyzers 40. As will be understood, this distribution 60 will normally be very close to the target distribution 50 based on the control action of the controller 42 executing the stored control program 46 to provide control signals 62 to each of the metering devices 20, 22, and 24.

Figure 3:
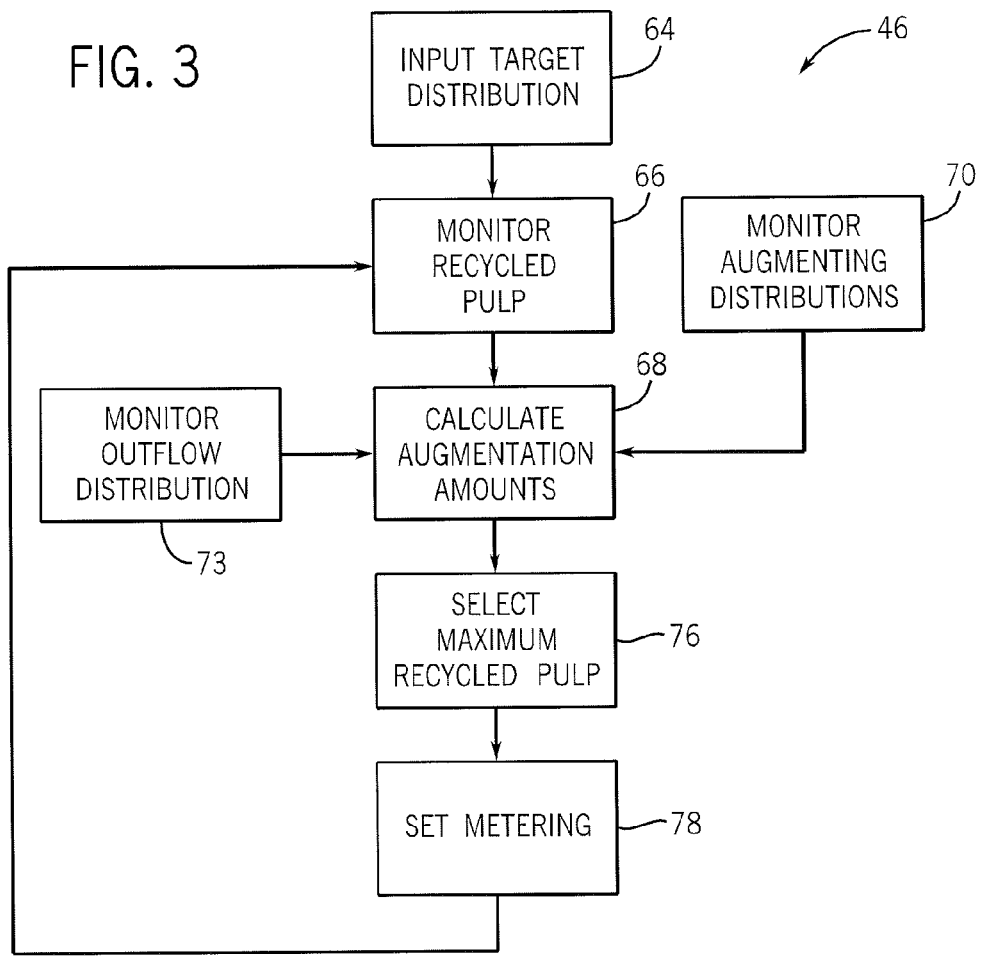
FIG. 3 is a block diagram of a program executed by the controller of FIG. 2 in determining the control signals provided to the control valves.

Referring now also to FIG. 3, the control program 46 starts, as indicated by process block 64, by accepting the command data set 48. This command data set 48 may be entered manually based on empirically discovered formulas for paper or may be selected from a pre-existing library of formulas.

At process block 64, the distribution 56 from the online pulp fiber analyzer 31 monitoring the recycled pulp source 14 is read and at succeeding process block 68, amounts of augmenting pulp from pulp sources 12 and 16 are calculated based on current measurements of those pulps, taken at process block 70, using online pulp fiber analyzers 30 and 32. The positioning of the pulp fiber analyzer 31 may be upstream of the metering devices 20, 22, and 24 and of the introduction of the pulp into the mixing cabinet 26 to provide for sufficient calculation time to control metering devices 20, 22, and 24 for the right augmenting fiber addition.

The calculation of the necessary amounts of augmenting pulp from pulp sources 12 and 16 may be done by characterizing each of the distributions by one or more moments and using an algebraic decomposition, for example, as described in Ring, Gerard, J. F.; Bacon, Aric J., "Multiple-Component Analysis of Fiber Length Distributions", *TAPPI Journal*, Vol. 78, No. 7, pp. 224-231 (1997). Particularly when multiple-augmenting fiber sources are used, other calculation techniques may also be used, for example, those employing hill climbing techniques, or Monte Carlo or simulated annealing techniques. The predicted distribution of the mixed fibers will be a bin-by-bin summing of the distributions of each of the pulp sources 12, 14, and 16 weighted by their percentage representation in the mix established by the control of metering devices 20, 22, and 24.

The mix of the pulp from the pulp sources 12, 14 and 16 may be further adjusted according to the monitored outflow distribution from fiber analyzer 40 per process block 73 to accommodate errors between the target distribution 50 and the output of the fiber analyzer 40 caused by the action of the mixing chamber or other systematic offsets.

Figure 4:
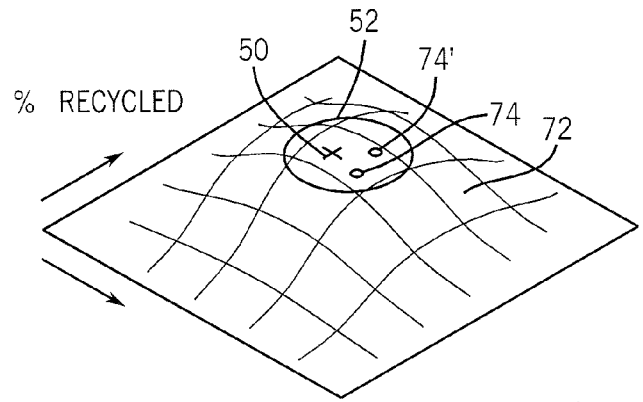
FIG. 4 is a graphic representation of the control space for two control dimensions showing a strategy of maximizing use of one pulp source while in optimizing the pulp uniformity.

Referring now to FIG. 4, the calculation of process block 68 produces multiple solutions 74 on a solution surface 72. These multiple solutions may, for example, lie within the error bands 52 about a given target distribution 50, or may be the result of different combinations of pulp from different tanks, providing competing solutions.

Under these circumstances, a particular solution 74' may be selected so as to maximize the amount of recycled fiber used in the stock per process block 76 or alternately to maximize use of the most cost-effective fiber source and to minimize more costly fiber sources.

Finally, at process block 78, metering devices 20, 22, and 24 are set.

Upon completion of the setting of the metering devices 20, 22, and 24, the control program 46 cycles again to process block 66 to repeat these steps.

Metering device 36 may be controlled according to the desired delivery rate of pulp but may also be adjusted to control the dwell time of pulp within the mixing cabinet 26 to improve the mixing as may be determined by monitoring variations in the pulp distribution 60.

In alternative embodiments, other physical fiber parameters such as curl or coarseness maybe be monitored by the pulp fiber analyzers 30, 31 and 32 instead of fiber length, and pulp sources 12 and 16 may hold pulp sources selected to provide appropriately skewed fiber distributions to allow for correction of curl or coarseness.

Figure 5:
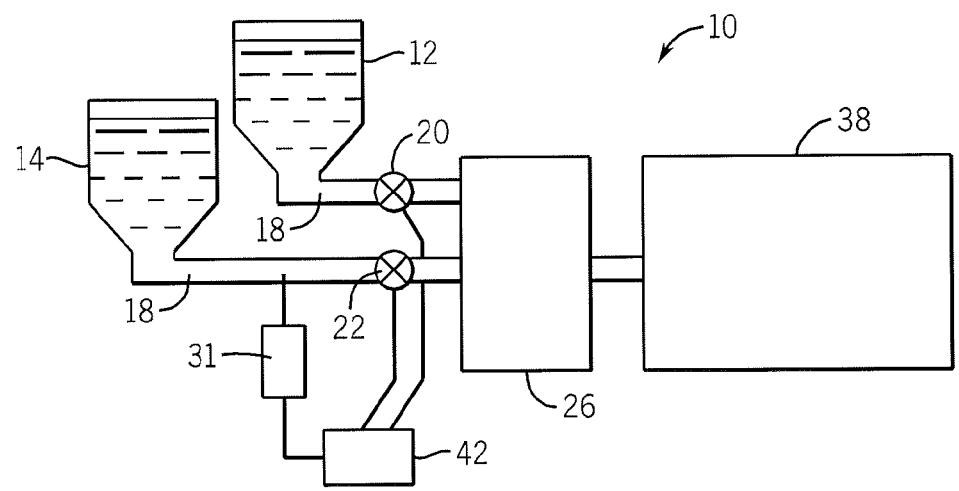
FIG. 5 is an alternative embodiment of the pulp pre-processor employing a single pulp fiber analyzer.

Referring now to FIG. 5, a simplified embodiment of the invention may, for example, include two pulp sources 14 and 12 and a single pulp fiber analyzer 31. In this case, the pulp in pulp source 12 is pre-characterized, for example, by pulp fiber analyzer 31 before start of the pre-processing, after which the pulp fiber analyzer 31 is switched over to pulp source 12 for real-time monitoring of the pulp source 14. The initial distribution of the fibers in pulp source 12 is provided to the controller 42 and it is assumed the pulp from pulp source 12 is essentially homogenous and invariant.

Otherwise, a similar control strategy as that described above may be adopted, however, with a lesser ability to correct for distribution deficiencies in the recycled pulp source 14. Even so, the simplified pulp pre-processor 10 of FIG. 5, by providing precise metering of the augmenting pulp from pulp sources 12, can potentially provide a high-quality and uniform-quality paper pulp with a large percentage of recycled fibers and efficient conservation of un-recycled fibers from pulp source 12.

Figure 6:
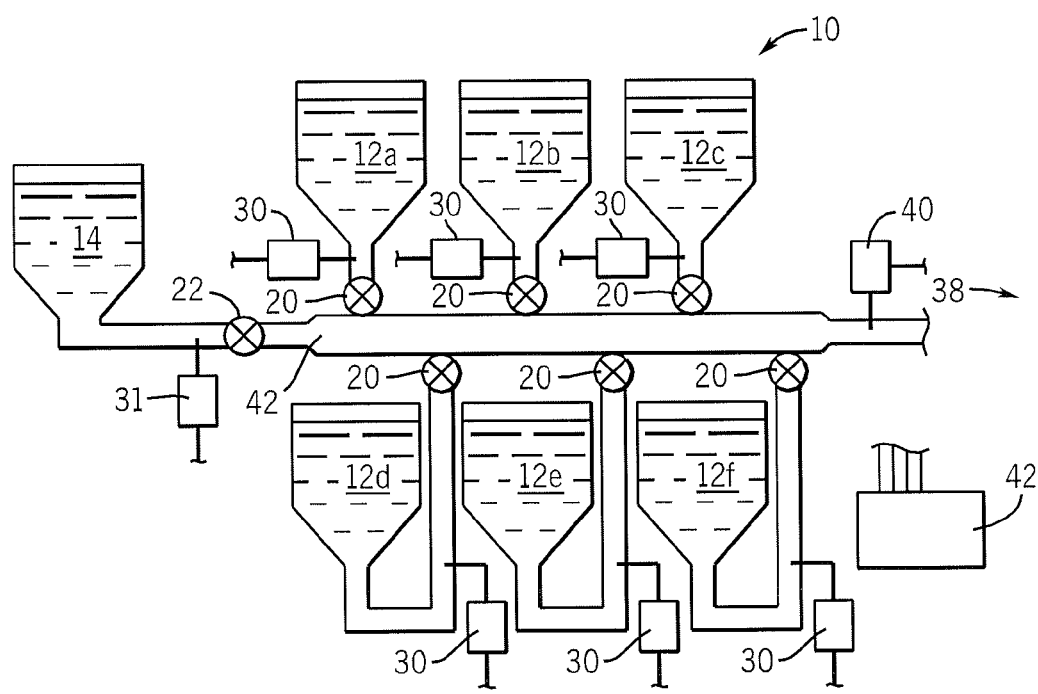
FIG. 6 is an alternative embodiment of the pre-processor of FIG. 1 providing for multiple dimensions of fiber augmentation.

Referring now to FIG. 6, a multi-dimensional pulp pre-processor 10 may make use of a pulp source 14 and six augmenting pulp sources 12a through 12f, each with corresponding metering devices 20 and pulp fiber analyzers 30, all under the control of controller 42. In this case, each of the augmenting pulp sources 12a through 12f may be selected to have polar distributions of a given physical pulp parameter, for example, long fiber length, short fiber length, high fiber curl, low fiber curl, fine fibers and coarse fibers. The controller 42 may thus affect multiple control loops to correct the distribution of pulp source 14 for any of these parameters.

This pulp pre-processor 10 provides bi-directional parameter control and thus potentially can handle a wide range recycled pulp from pulp source 14 providing uniform output pulp while incorporating a large percentage of recycled pulp into the resultant mixed pulp.

It will be understood that alternatively, each of the pulp sources 12a through 12f may represent different polar combinations of pairs of the parameters so that appropriate combinations of the pulp from these tanks can still effect arbitrary bi-directional correction of any distribution of fiber parameters.

The pulp sources 12a through 12f may be selected from pulps of particular wood species or may, in fact, be pulp sources that have been pre-processed to accentuate the desired characteristics. For example, a pulp source with a fiber length distribution weighted toward long fibers can be prepared through centrifugal separation or other known techniques.

It will be understood that the present process is not limited strictly to use with recycled fibers but may also be used to provide for extremely uniform pulp for exacting papermaking processes or to handle variations in un-recycled pulp sources. Further it will be recognized that multiple fiber analyzers can in fact be implemented with a single computational or optical unit shared among pulp streams so that separate real time measurements are nevertheless obtained.

It is specifically intended that the present invention not be limited to the embodiments and illustrations contained herein, but include modified forms of those embodiments including portions of the embodiments and combinations of elements of different embodiments as come within the scope of the following claims.

What I claim is:
1. A pulp pre-processor for papermaking comprising:
a mixing chamber having an outlet for providing pulp having a desired predetermined statistical distribution to a papermaking machine, the desired predetermined statistical distribution providing multipoint data describing a target histogram of a physical parameter of pulp desired for use in paper making;
at least two pulp sources communicating with the mixing chamber by controllable metering devices;
at least two electronic pulp fiber analyzers associated with each of the two pulp sources to provide corresponding signals measuring a statistical distribution of at least one physical parameter of fibers of the pulp sources as delivered to the mixing chamber the statistical distribution outputting multipoint data describing a pulp source histogram of the physical parameter;

an electronic pulp fiber analyzer associated with the mixing chamber to provide a corresponding signal measuring a statistical distribution of at least one physical parameter of combined fibers of the pulp sources as delivered from the mixing chamber the statistical distribution outputting multipoint data describing a mixing chamber histogram of the physical parameter and a controller executing a stored program receiving the target histogram, the pulp source histograms and the mixing chamber histogram to determine an error between the target histogram and the mixing chamber histogram, and further, by a summing of the multipoint data of the pulp source histograms on a bin by bin basis weighted by a percentage of the pulp introducible in the mixing chamber from each corresponding pulp source, calculating a relative percentage of fiber of the at least two pulp sources necessary to produce the target histogram delivered from the mixing chamber and providing real-time control signals to the metering devices to control them according to the calculated relative percentage.

2. The pulp pre-processor of claim 1 wherein one source provides a distribution of fiber lengths relative to the other source that is skewed toward longer fiber lengths and wherein the electronic pulp fiber analyzers provide signals measuring statistical distributions of fiber length.

3. The pulp pre-processor of claim 1 wherein one source provides a distribution of curl relative to the other source that is skewed toward greater fiber curl and wherein the electronic pulp fiber analyzers provide signals measuring statistical distributions of fiber curl.

4. The pulp pre-processor of claim 1 wherein one source provides a distribution of fiber coarseness relative to the other source that is skewed toward greater fiber coarseness and wherein the electronic pulp fiber analyzers provide signals measuring statistical distributions of fiber coarseness.

5. The pulp pre-processor of claim 1 further including a third source and a third controllable metering device leading to the mixing chamber and a third electronic pulp fiber analyzer providing a third signal measuring a statistical distribution of at least one physical parameter of fibers of the pulp as delivered to the mixing chamber; wherein the controller further controls the relative proportions of the pulp from the three sources based on the desired predetermined statistical distribution.

6. The pulp pre-processor of claim 5 wherein the controller further controls the relative proportions of the pulp from the two sources based on the third signal to maximize use of the third source within a constraint of the desired predetermined statistical distribution.

7. The pulp pre-processor of claim 5 wherein the first and second sources have physical parameters of fibers with distributions skewed in opposite directions from an anticipated distribution of physical parameters of fibers from the third source.

* * * * *